US006524560B1

(12) United States Patent
Prechtl et al.

(10) Patent No.: US 6,524,560 B1
(45) Date of Patent: Feb. 25, 2003

(54) USE OF SUBSTITUTED VINYLTETRAHYDRONAPHTHALENES AND VINYL-BENZOTETRAHYDROPYRANS AS LIGHT PROTECTION AGENTS

(75) Inventors: Frank Prechtl, Frankfurt (DE); Thorsten Habeck, Meckenheim (DE); Horst Westenfelder, Neustadt (DE); Thomas Wünsch, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/583,760

(22) Filed: May 31, 2000

(30) Foreign Application Priority Data

Jun. 11, 1999 (DE) ......................... 199 26 779

(51) Int. Cl.$^7$ ............... A61K 7/42; A61K 7/44; A61K 9/00; A61K 6/00
(52) U.S. Cl. .................. 424/59; 424/59; 424/60; 424/400; 424/401
(58) Field of Search .................. 424/59, 60, 400, 424/401

(56) References Cited

U.S. PATENT DOCUMENTS

| 4,387,089 A | | 6/1983 | DePolo ............... 424/59 |
| 4,950,467 A | | 8/1990 | Phalangas et al. ....... 424/59 |
| 5,508,025 A | * | 4/1996 | Hoshino et al. ......... 424/59 |
| 5,576,354 A | | 11/1996 | Deflandre et al. ....... 514/685 |
| 5,587,150 A | | 12/1996 | Deflandre et al. ....... 424/59 |

FOREIGN PATENT DOCUMENTS

| EP | 251 398 | 1/1988 |
| EP | 514 491 | 11/1992 |
| FR | 2 440 933 | 6/1980 |
| WO | WO 91/11989 | 8/1991 |

* cited by examiner

Primary Examiner—Jose' G. Dees

(74) Attorney, Agent, or Firm—Keil & Weinkauf

(57) ABSTRACT

The invention relates to the use of compounds of the formula I in which
- X is the divalent radical of oxygen, a carbonyl radical, optionally aliphatically substituted imino or the radical $=CR^9R^{10}$,
- Y is a carbonyl group or the radical $=CR^9R^{10}$,
- $R^1$ and $R^2$ are identical or different electron-withdrawing radicals, chosen from the group consisting of cyano, alkyl- or arylcarbonyl, alkyloxy- or aryloxycarbonyl, optionally substituted aminocarbonyl, alkyl- or arylsulfinyl, alkyl- or arylsulfonyl and optionally substituted aminosulfonyl,
- $R^3$ is a hydrogen atom, a cyano, hydroxyl, carboxyl or aminocarbonyl group or a $C_5$–$C_{20}$-aryl radical or $C_1$–$C_{20}$-alkylradical optionally bonded via an oxygen bridge, an aminocarbonyl bridge or oxycarbonyl bridge,
- $R^4$ is a hydrogen atom, a hydroxyl group, an amino group, or a $C_5$–$C_{20}$-aryl radical or $C_1$–$C_{20}$-alkyl radical optionally bonded via an oxygen bridge, and
- $R^5$ to $R^{10}$ independently of one another are hydrogen or $C_1$–$C_{20}$-alkyl radicals and where in addition $R^7$ and $R^8$ together with the chain carbon atom are a carbonyl group, as photostable UV filters in cosmetic and pharmaceutical preparations for protecting human skin and human hair from solar rays, alone or together with compounds which absorb in the UV region and are known per se for cosmetic and pharmaceutical preparations.

8 Claims, No Drawings

USE OF SUBSTITUTED VINYLTETRAHYDRONAPHTHALENES AND VINYL-BENZOTETRAHYDROPYRANS AS LIGHT PROTECTION AGENTS

The invention relates to the use of vinyl-substituted tetrahydronaphthalenes or benzotetrahydropyrans which carry electron-withdrawing substituents on the vinyl radical, as light protection agents in cosmetic and pharmaceutical preparations and as light protection additives in plastics. The invention further relates to novel compounds of said type which have a light protection action and which carry cyano groups as electron-withdrawing substituents.

The light protection agents used in cosmetic and pharmaceutical preparations have the task of preventing, or at least diminishing the consequences of, harmful effects of sunlight on the human skin. However, these light protection agents also serve to protect other ingredients from decomposition or breakdown by UV radiation. In hair cosmetic formulations the aim is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancers in areas of strong solar radiation shows that damage to the genetic information in the cells is evidently also caused by sunlight, specifically by UV-A radiation. All these findings would therefore suggest that it is necessary to develop efficient filter substances for the UV-A region.

There is a growing demand for light protection agents for cosmetic and pharmaceutical preparations which can be used in particular as UV-A filters and whose absorption maxima ought therefore to be in the range from about 320 to 380 nm. In order to achieve the desired effect using the minimum amount, light protection agents of this type should additionally have a high specific absorbance. Light protection agents for cosmetic preparations must also meet a large number of other requirements, for example good solubility in cosmetic oils, high stability of the emulsions prepared therewith, toxicological acceptability and low intrinsic odor and low intrinsic color.

Another requirement which light protection agents must meet is adequate photostability. However, this is only inadequately ensured, if at all, with the UV-A-absorbing light protection agents available hitherto.

French Patent No. 2 440 933 describes 4-(1,1-dimethylethyl)-4'-methoxydibenzoylmethane as a UV-A filter. It is proposed to combine this particular UV-A filter, which is sold by GIVAUDAN under the name "PARSOL 1789", with various UV-B-filters in order to absorb all UV rays having a wavelength from 280 to 380 nm. However, this UV-A filter does not have sufficient photochemical stability, when used alone or in combination with UV-B filters, to ensure sustained protection of the skin during sunbathing for extended periods, which means that repeated applications at regular and short intervals are required if effective protection of the skin from all UV rays is desired.

For this reason, EP-A-0 514 491 discloses the stabilization of the insufficiently photostable UV-A filters by adding 2-cyano-3,3-diphenylacrylic esters, which themselves act as filters in the UV-B region.

Furthermore, it has already been proposed in EP-A-0 251 398 to combine chromophores which absorb UV-A radiation and UV-B radiation into a molecule via a linker. This has the disadvantage that firstly it is no longer possible to freely combine UV-A and UV-B filters in the cosmetic preparation, and that difficulties in the chemical linkage of the chromophores permit only certain combinations.

U.S. Pat. No. 4,950,467 describes the use of 2,4-pentadienoic acid derivatives as UV absorbers in cosmetic preparations. The monoaryl-substituted compounds specified in this patent specification as being preferable likewise have the disadvantage that their photostability is insufficient.

It is an object of the present invention to propose light protection agents for cosmetic and pharmaceutical purposes which absorb predominantly in the UV-A region (and optionally alternatively in the UV-B region) with high absorbance, are photostable, have low intrinsic color, i.e. a sharp band structure, and are soluble in oil or water depending on the substituent.

We have found that this object is achieved according to the invention by the use of compounds of the formula I

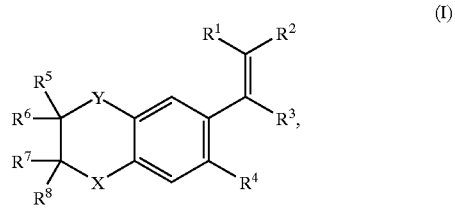

(I)

in which
   X is the divalent radical of oxygen, a carbonyl radical, optionally aliphatically substituted imino or the radical $=CR^9R^{10}$,
   Y is a carbonyl group or the radical $=CR^9R^{10}$,
   $R^1$ and $R^2$ are identical or different electron-withdrawing radicals, chosen from the group consisting of cyano, alkyl- or arylcarbonyl, alkyloxy- or aryloxycarbonyl, optionally substituted aminocarbonyl, alkyl- or arylsulfinyl, alkyl- or arylsulfonyl and optionally substituted aminosulfonyl,
   $R^3$ is a hydrogen atom, a cyano, hydroxyl, carboxyl or aminocarbonyl group or a $C_5$–$C_{20}$-aryl radical or $C_1$–$C_{20}$-alkyl radical optionally bonded via an oxygen bridge, an aminocarbonyl bridge or oxycarbonyl bridge,
   $R^4$ is a hydrogen atom, a hydroxyl group, an amino group, or a $C_5$–$C_{20}$-aryl radical or $C_1$–$C_{20}$-alkyl radical optionally bonded via an oxygen bridge, and
   $R^5$ to $R^{10}$ independently of one another are hydrogen or $C_1$–$C_{20}$-alkyl radicals and where in addition $R^7$ and $R^8$ together with the chain carbon atom are a carbonyl group, as photostable UV filters in cosmetic and pharmaceutical preparations for protecting human skin and human hair from solar rays, alone or together with compounds which absorb in the UV region and are known per se for cosmetic and pharmaceutical preparations.

The alkyl radicals in the substituents $R^1$ and/or $R^2$ generally have from 1 to 20 carbon atoms and are preferably low molecular weight alkyl radicals having from 1 to 8 carbon atoms and are, in particular, methyl radicals.

The aryl radicals in the substituents $R^1$ and/or $R^2$ are isocyclic or heterocyclic radicals having from 5 to 10 ring atoms and from 3 to 20 carbon atoms, such as phenyl, naphthyl, pyridyl, thiazinyl or furanyl, which can be further substituted.

Alkyl radicals for $R^3$ and $R^4$ and $R^5$ to $R^{10}$ are preferably low molecular weight radicals having from 1 to 5 carbon atoms, preferably methyl. $R^3$ and/or $R^4$ as aryl radical is generally a mono- or binuclear isocyclic or heterocyclic radical, which can also be further substituted. Examples are phenyl, naphthyl, pyridyl, thiazinyl or furanyl.

Of the compounds of the formula I, preference is given to those in which $R^3$ to $R^8$ are hydrogen and X and Y are $=CR^9R^{10}$, where $R^9$ and $R^{10}$ are hydrogen or low molecular weight alkyl radicals having from 1 to 5 carbon atoms or $R^3$ to $R^8$ are hydrogen and X is oxygen and Y is $=CR^9R^{10}$, where $R^9$ and $R^{10}$ are hydrogen or alkyl radicals having from 1 to 5 carbon atoms.

Particular preference is given to compounds of the formula I in which $R^1$ and/or $R^2$ are the radicals ethoxycarbonyl, acetyl or cyano, $R^3$ is hydrogen or methyl-, $R^4$ is hydrogen or methyl-, $R^5$ to $R^8$ are hydrogen, X is oxygen or $=C(CH_3)_2$ and Y is $=CH_2$ or $=C(CH_3)_2$.

Of the compounds of the formula I, compounds of the formula II

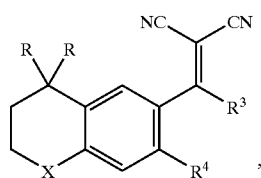

(II)

in which $R^3$ is a low molecular weight alkyl radical, $R^4$ is hydrogen, a low molecular weight alkyl radical or a low molecular weight alkoxy radical, X is the divalent radical of oxygen or the radical $=CRR$, where R is hydrogen or low molecular weight alkyl, are novel and are therefore claimed as new substances.

The compounds of the formula I or II are obtained in a manner known per se by reaction of compounds of the formula III $R^1$—$CH_2$—$R^2$ with the substituted benzaldehydes of the formula IV

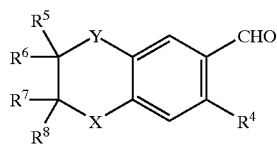

(IV)

where $R^1$ to $R^8$ are as defined above.

The aldehydes of the formula IV are described in detail in the literature and can be obtained by oxidation of a methyl group or by a Vilsmeier reaction.

The condensation to give the known compounds of the formula I or II is carried out in a manner known per se by a Knoevenagel condensation of a CH-azidic compound such as, for example, diethyl malonate, with the corresponding naphthylaldehyde and with catalytic amounts of ammonium acetate/acetic acid in a solvent such as methylene chloride, cyclohexane, toluene or xylene, which, with the water of reaction which is produced, forms an azeotrope which can be distilled off. The reaction temperatures are governed by the boiling point of the solvent used and the reactivity of the carbonyl compound. In the same way it is also possible to prepare the novel condensates using malodinitrile; here, it is possible to partly dispense with the addition of a water-entraining solvent.

The present invention further relates to cosmetic and pharmaceutical preparations which comprise from 0.1 to 10% by weight, preferably from 1 to 7% by weight, based on the total amount of the cosmetic and pharmaceutical preparation, of one or more of the compounds of the formula I together with compounds which absorb in the UV-A and UV-B region and are known per se for cosmetic and pharmaceutical preparations as light protection agents, where the compounds of the formula I are generally used in a lesser amount than the UV-B-absorbing compounds.

The cosmetic and pharmaceutical preparations which comprise light protection agents are usually based on a carrier which comprises at least one oil phase. However, preparations merely based on water are also possible if compounds with hydrophilic substituents are used. Accordingly, suitable preparations are oil, oil-in-water and water-in-oil emulsions, creams and pastes, lipcare stick compositions or grease-free gels.

Sunscreen preparations of this type can, accordingly, be in liquid, paste or solid form, for example as water-in-oil creams, oil-in-water creams and lotions, aerosol foam creams, gels, oils, wax pencils, powders, sprays or alcoholic-aqueous lotions.

Examples of customary oil components in cosmetics are paraffin oil, glyceryl stearate, isopropyl myristate, diisopropyl adipate, cetyl stearyl 2-ethylhexanoate, hydrogenated polyisobutene, Vaseline, capryllic/capric triglycerides, microcrystalline wax, lanolin and stearic acid.

Customary cosmetic auxiliaries which may be suitable as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are preferably known W/O and also O/W emulsifiers such as, for example, polyglycerol esters, sorbitan esters or partially esterified glycerides. Typical examples of fats are glycerides; waxes which may be mentioned are, inter alia, beeswax, paraffin wax or microwaxes, possibly in combination with hydrophilic waxes. Stabilizers which can be used are metal salts of fatty acids such as, for example, magnesium, aluminum and/or zinc stearate. Suitable thickeners are, for example, crosslinked polyacrylic acids and derivatives thereof, polysaccharides, in particular xanthan gum, guar guar, agar agar, alginates and tyloses, carboxylmethylcellulose and hydroxyethylcellulose and also fatty alcohols, monoglycerides and fatty acids, polyacrylates, polyvinyl alcohol and polyvinylpyrrolidone. Examples of biogenic active ingredients are plant extracts, protein hydrolysates and vitamin complexes. Examples of customary film formers are hydrocolloids such as chitosan, microcrystalline chitosan or quaternized chitosan, polyvinyl pyrrolidone, vinylpyrrolidone-vinyl acetate copolymers, polymers of the acrylic acid series, quaternary cellulose derivatives and similar compounds. Examples of suitable preservatives are formaldehyde solution, p-hydroxybenzoate or sorbic acid. Examples of pearlizing agents are glycol distearic esters such as ethylene glycol distearate, but also fatty acids and fatty acid monoglycol esters. Dyes which can be used are the substances suitable and approved for cosmetic purposes, as listed, for example, in the publication "Kosmetische Farbemittel" [Cosmetic Colorants] from the Farbstoffkommission der Deutschen Forschungsgemeinschaft, [Dyes Commission of the German Research Society], published in Verlag Chemie, Weinheim, 1984. These dyes are normally used in concentrations of from 0.001 to 0.1% by weight, based on the total mixture.

The total content of auxiliaries and additives can be from 1 to 80% by weight, preferably from 6 to 40% by weight, and the nonaqueous content ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Finally, it is also possible to co-use other substances which absorb in the UV region and are known per se, as long as they are stable in the overall system of the combination of UV filters to be used according to the invention.

Most of the light protection agents in the cosmetic and pharmaceutical preparations used for protecting the human epidermis consist of compounds which absorb UV light in the UV-B region, i.e. in the range from 280 to 320 nm. For example, the content of the UV-A absorbers to be used according to the invention is from 10 to 90% by weight, preferably from 20 to 50% by weight, based on the total amount of UV-B and UV-A absorbing substances.

The UV filter substances used in combination with the compounds of the formula I to be used according to the invention are any UV-A and UV-B filter substances. Examples which may be mentioned are:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3,'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71671-10-2 |
| 11 | 2-Ethylhexyl 4-methoxycinnamate | 5466-77-3 |
| 12 | 2-Hydroxy-4-methoxybanzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenbornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianilino(o-carbo-2'-ethylhe-xyl-1'-oxy)-1,3,5-triazine | 88122-99-0 |
| 18 | 3-Imidazol-4-yl-acrylic acid and its ethyl ester | 104-98-3 |
| 19 | Menthyl o-aminobenzoate or: 5-methyl-2-(1-methylethyl) 2-aminobenzoate | 134-09-8 |
| 20 | Glyceryl p-aminobenzoate or:1-glyceryl 4-aminobenzoate | 136-44-7 |
| 21 | 2,2'-Dihydroxy-4-methoxybenzophenone(dioxybenzone) | 131-53-3 |
| 22 | 2-Hydroxy-4-methoxy-4-methylbenzophenone (Mexenone) | 1641-17-4 |
| 23 | Triethanolamine salicylate | 2174-16-5 |
| 24 | Dimethoxyphenylglyoxalic acid or: sodium 3,4-dimethoxyphenylglyoxalate | 4732-70-1 |
| 25 | 3-(4'-Sulfobenzylidene)bornan-2-one and its salts | 56039-58-8 |
| 26 | 2,2',4,4'-Tetrahydroxybenzophenone | 131-55-5 |

-continued

| No. | Substance | CAS No. (=acid) |
|---|---|---|
| 27 | 2,2'-Methylenebis[6(2H-benzotriazol-2-yl)-4-(1,1,3,3,-tetramethylbutyl)phenol] | 103597-45-1 |
| 28 | 2,2'-(1,4-Phenylene)bis-1H-benzimidazole-4,6-disulfonic acid, Na salt | 180898-37-7 |
| 29 | 2,4-bis[4-(2-Ethylhexyloxy)-2-hydroxy]phenyl-6-(4-methoxyphenyl)-(1,3,5)-triazine | 187393-00-6 |
| 30 | 3-(4-Methylbenzylidene)camphor | 36861-47-9 |
| 31 | Polyethoxyethyl 4-bis(poly-ethoxy) paraaminobenzoate | 113010-52-9 |
| 32 | 2,4-Dihydroxybenzophenone | 131-56-6 |
| 33 | 2,2'-Dihydroxy-4,4'-dimethoxybenzophenone-5,5'-disodium sulfonate | 3121-60-6 |

Finally, mention may also be made of micronized pigments such as titanium dioxide and zinc oxide.

To protect human hair from UV rays, the light protection agents of the formula I according to the invention can be incorporated into shampoos, lotions, gels, hairsprays, aerosol foam creams or emulsions in concentrations of from 0.1 to 10% by weight, preferably from 1 to 7% by weight. The particular formulations can be used, inter alia, for washing, coloring or for styling the hair.

The compounds to be used according to the invention usually have a particularly high absorbance in the region of UV-A radiation with a sharp band structure. Furthermore, they are readily soluble in cosmetic oils and can be readily incorporated into cosmetic formulations. The emulsions prepared using the compounds I are notable in particular for their high stability, the compounds I themselves have high photostability, and the preparations produced using I have a pleasant feel on the skin.

The UV filter action of the compounds of the formula I according to the invention can also be utilized for stabilizing active ingredients and auxiliaries in cosmetic and pharmaceutical formulations.

The compounds according to the invention are highly suitable for stabilizing organic materials against the effect of light, oxygen and heat.

Examples of plastics which can be stabilized by the compounds I according to the invention which may be mentioned are:

polymers of mono- and diolefins, such as, for example, low or high density polyethylene, polypropylene, linear polybut-1-ene, polyisoprene, polybutadiene and copolymers of mono- or diolefins or mixtures of said polymers;

copolymers of mono- or diolefins with other vinyl monomers, such as, for example, ethylene-alkyl acrylate copolymers, ethylene-alkylmethacrylate copolymers, ethylene-vinylacetate copolymers or ethylene-acrylic acid copolymers;

polystyrene and copolymers of styrene or α-methylstyrene with dienes and/or acrylic derivatives, such as, for example, styrene-butadiene, styrene-acrylonitrile (SAN), styrene-ethyl methacrylate, styrene-butadiene -ethyl acrylate, styrene-acrylonitrile-methacrylate, acrylonitrile-butadiene-styrene (ABS) or methylmethacrylate-butadiene-styrene (MBS);

halogen-containing polymers, such as, for example, polyvinyl chloride, polyvinyl fluoride, polyvinylidine fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines and from their acrylic derivatives or acetals, e.g. polyvinyl alcohol and polyvinyl acetate;

polyurethanes, polyamides, polyureas, polyphenylene ethers, polyesters, polycarbonates, polyoxymethylenes, polysulfones, polyether sulfones and polyether ketones.

The compounds I according to the invention can also be used to stabilize surface coatings, e.g. industrial coatings. Of these, particular emphasis is given to stoving finishes, and of these, in turn, automotive finishes, preferably two-coat finishes.

The compounds I according to the invention can be added to the coating in solid or dissolved form. In this context, their ready solubility in coating systems is of particular advantage.

Preference is given to using the compounds I according to the invention for stabilizing polyolefins, in particular polyethylene, polycarbonates, polyamides, polyesters, polystyrene, ABS and polyurethanes. In particular, it is also possible to stabilize films made of said plastics.

For these fields of use, the compounds are used in concentrations of from 0.01 to 5% by weight, based on the amount of plastic, preferably in a concentration of from 0.02 to 2% by weight. The combination with other stabilizers, for example antioxidants, metal deactivators or other light protection agents, and with antistatic or flame-inhibiting agents, is often advantageous. Particularly important costabilizers are, for example, sterically hindered phenols and phosphites, phosphonites, amines and sulfur compounds.

Examples of suitable costabilizers are:

phenolic antioxidants such as 2,6-di-tert-butyl-4-methylphenol, n-octadecyl B-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl) benzene, 1,3,5-tris(3,5-di-tert-butyl-4-hydroxybenzyl) isocyanurate, 1,3,5-tris[β-(3,5-di-tert-butyl-4-hydroxyphenyl)propionylethyl] isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxy)propionate], phosphorus-containing antioxidants such as tris (nonylphenyl) phosphite, distearylpentaerythritol phosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl)-4,4'-biphenylenediphosphite, sulfur-containing antioxidants such as dilauryl thiodipropionate, dimyristyl thiodipropionate, distearyl thiodipropionate, pentaerythritol tetrakis(β-laurylthiopropionate) and pentaerythritol tetrakis(β-hexylthiopropionate), sterically hindered amines such as bis(2,2,6,6-tetramethylpiperidyl) sebacate, bis(1,2,2,6,6-pentamethylpiperidyl) sebacate, bis(1,2,2,6,6-pentamethylpiperidyl) ester, N,N'-bis(formyl)bis(2,2,6,6-tetramethyl-4-piperidyl)-1,6-hexanediamine, the condensation product of 1-hydroxy-2,2,6,6-tetramethyl-4-hydroxypiperidine and succinic acid, the condensation product of
N,N'-(2,2,6,6-tetramethylpiperidyl) hexamethylenediamine and 4-tert-octylamino-2,6-dichloro-1,3,5-s-triazine, poly[3-(eicosyl/tetracosyl)-1-(2,2,6,6-tetramethylpiperidin-4-yl)pyrrolidin-2,5-dione], tris(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanediyl)bis(3,3,5,5-tetramethylpiperazinone), the condensation products of 4-amino-2,2,6,6-tetramethylpiperidines and tetramethylolacetylenediureas, and 2-(2'-hydroxyphenyl)benzotriazoles, 2-hydroxybenzophenones, aryl esters of hydroxybenzoic acids, α-cyanocinnamic acid derivatives, nickel compounds or oxalic dianilides.

For mixing the compounds I according to the invention, especially with plastics, it is possible to use all known equipment and methods for incorporating stabilizing agents or other additives into polymers.

EXAMPLES

Example 1

(Preparation)

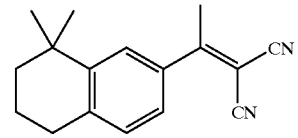

19.2 g (0.094 mol) of 6-acetyl-4,4-dimethyl-3,4-dihydro-2H-1-benzopyran, 6.6 g (0.1 mol) of malodinitrile, 1.0 g of ammonium acetate and 7.0 g of glacial acetic acid are mixed in a flask and stirred for 3 h at 120° C. After cooling, the product is purified by column chromatography (silica gel, cyclohexane/ethyl acetate 4:1). This gives, as product, 6.7 g (28%) of a yellowish oil ($\lambda_{max}$: 346 nm, $E^1/1$: 694, photostability 30 min/2h: 96%/90%).

Similarly, the compounds in Table 1 below are excellent light protection agents.

| Example No. | Structure | $\lambda_{max}$ [nm] | $E^1/1$ | Photostability [%] 30 min/2 h |
|---|---|---|---|---|
| 2 | 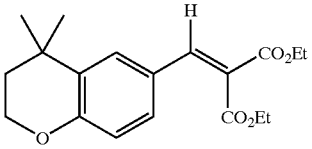 | 320 | 616 | 100/95 |

-continued

| Example No. | Structure | $\lambda_{max}$ [nm] | $E^1/1$ | Photostability [%] 30 min/2 h |
|---|---|---|---|---|
| 3 | *chroman with CH=C(COMe)(COMe) substituent* | 330 | 801 | 97/84 |
| 4 | *tetramethyltetralin with Me and CH=C(CN)(CN) substituents* | 336 | 700 | 95/83 |
| 5 | *tetramethyltetralin with CH=C(CN)(C(O)CMe₃) substituent* | 330 | 601 | 86/83 |
| 6 | *tetramethyltetralin with CH=C(CO₂Et)(CO₂Et) substituent* | 294 | 411 | 100/99 |
| 7 | *tetramethyltetralin with Me and CH=C(CO₂Et)(CO₂Et) substituents* | 294 | 594 | 99/95 |
| 8 | *tetramethyltetralin with OMe and CH=C(CO₂Et)(CO₂Et) substituents* | 335 / 288 | 248 / 377 | 100/100 |

Example 9
Standardized Method for Determining Photostability (Sun Test)

A 5% strength by weight alcoholic solution of the light protection agent to be tested is applied, using an Eppendorf pipette (20 µl), to the milled area of a small glass plate. Owing to the presence of the alcohol, the solution distributes uniformly on the roughened surface of the glass. The amount applied corresponds to the amount of light protection agent required to achieve an average sun protection factor in suncreams. In the test, four small glass plates are irradiated in each case. The evaporation time and the irradiation each last for 30 minutes. The small glass plates are cooled slightly during irradiation using a water cooling system located at the base of the sun test apparatus. The temperature inside the sun test apparatus is 40° C. during irradiation. After the samples have been irradiated, they are washed with ethanol in a dark 50 ml graduated flask and measured using a photometer. The blank samples are likewise applied to small glass plates and evaporated at room temperature for 30 minutes. Like the other samples, they are washed off with ethanol and diluted to 100 ml and measured.

Cosmetic Preparations:

Example 10
General procedure for the preparation of emulsions for cosmetic purposes All of the oil-soluble constituents are heated to 85° C. in a stirred vessel. When all of the constituents are molten or are in the form of a liquid phase, the aqueous phase is incorporated with homogenization. While being stirred, the emulsion is cooled to about 40° C., perfumed and homogenized and then cooled to 25° C. with continuous stirring.

Example 11

(Cosmetic Preparation)

| Mass content % by weight | |
|---|---|
| ad 100 | water |
| 8.00 | octyl methoxycinnamate |
| 8.00 | titanium dioxide |
| 6.00 | PEG-7 hydrogenated castor oil |
| 5.00 | Compound from Example 1 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 12

Lipcare Composition

| Mass content % by weight | |
|---|---|
| ad 100 | Eucerinum anhydricum |
| 10.00 | glycerol |
| 10.00 | titanium dioxide |
| 5.00 | compound from Example 1 |
| 8.00 | octyl methoxycinnamate |
| 5.00 | zinc oxide |
| 4.00 | castor oil |
| 4.00 | pentaerythritol stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 13

Sunblock Composition Containing Micropigments

| Mass content % by weight | |
|---|---|
| ad 100 | water |
| 10.00 | octyl methoxycinnamate |
| 6.00 | PEG-7 hydrogenated castor oil |
| 6.00 | titanium dioxide |
| 5.00 | compound from Example 1 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

Example 14

Grease-free Gel

| Mass content % by weight | |
|---|---|
| ad 100 | water |
| 8.00 | octyl methoxycinnamate |
| 7.00 | titanium dioxide |
| 5.00 | compound from Example 1 |
| 5.00 | glycerol |
| 5.00 | PEG-25 PABA |
| 1.00 | 4-methylbenzylidenecamphor |
| 0.40 | acrylate $C_{10}$–$C_{30}$-alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

Example 15

Suncream (SPF 20)

| Mass content % by weight | |
|---|---|
| ad 100 | water |
| 8.00 | octyl methoxycinnamate |
| 8.00 | titanium dioxide |
| 6.00 | PEG-7-hydrogenated castor oil |
| 5.00 | compound from Example 1 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 16

Sunmilk (SPF 6)

| Mass content % by weight | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound from Example 1 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

We claim:

1. A cosmetic preparation comprising light protection agents, for protecting the human epidermis or human hair from UV light in the range from 280 to 400 nm, which comprises, in a cosmetically suitable carrier, alone or together with compounds which absorb in the UV region and are known per se for cosmetic and pharmaceutical preparations, compounds of the formula I

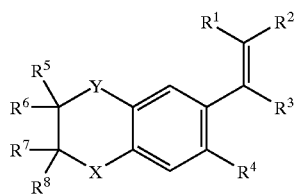

in which

X is the divalent radical of oxygen, a carbonyl radical, optionally aliphatically substituted imino or the radical $=CR^9R^{10}$, Y is a carbonyl group or the radical $=CR^9R^{10}$, $R^1$ and $R^2$ are identical or different electron-withdrawing radicals, chosen from the group consisting of cyano, alkyl- or arylcarbonyl,-alkyloxy- or aryloxycarbonyl, optionally substituted aminocarbonyl, alkyl- or arylsulfinyl, alkyl- or arylsulfonyl and optionally substituted aminosulfonyl, $R^3$ is a hydrogen atom, a cyano, hydroxyl, carboxyl or aminocarbonyl group or a $C_5$–$C_{20}$-aryl radical or $C_1$–$C_{20}$-alkyl radical optionally bonded via an oxygen bridge, an aminocarbonyl bridge or oxycarbonyl bridge, $R^4$ is a hydrogen atom, a hydroxyl group, an amino group, or a $C_5$–$C_{20}$-aryl radical or $C_1$–$C_{20}$-alkyl radical optionally bonded via an oxygen bridge, and $R^5$ to $R^{10}$ independently of one another are hydrogen or $C_1$–$C_{20}$-alkyl radicals and where in addition $R^7$ and $R^8$ together with the chain carbon atom are a carbonyl group.

2. A cosmetic preparation comprising light protection agents as claimed in claim 1, which comprises compounds of the formula I in which $R^3$ to $R^8$ are hydrogen and X and Y are $=CR^9R^{10}$, where $R^9$ and $R^{10}$ are hydrogen or low molecular weight alkyl radicals.

3. A cosmetic preparation comprising light protection agents as claimed in claim 1, which comprises compounds of the formula I in which $R^3$ to $R^8$ are hydrogen and X is oxygen and Y is $=CR^9R^{10}$, where $R^9$ and $R^{10}$ are hydrogen or alkyl radicals having from 1 to 5 carbon atoms.

4. A cosmetic preparation comprising light protection agents as claimed in claim 1, which comprises compounds of the formula I in which $R^1$ and/or $R^2$ are the radicals ethoxycarbonyl, acetyl or cyano, $R^3$ is hydrogen or methyl, $R^4$ is hydrogen or methyl, $R^5$ to $R^8$ are hydrogen, X is oxygen or $=C(CH_3)_2$ and Y is $=CH_2$ or $=C(CH_3)_2$.

5. A method for protecting the skin from the effects of UV radiation which comprises applying to the skin an effective amount of a composition as claimed in claim 1.

6. A method for protecting the skin from the effects of UV radiation as claimed in claim 5, wherein $R^3$ to $R^8$ are hydrogen, and X and Y are $=CR^9R^{10}$, where $R^9$ and $R^{10}$ are hydrogen or low molecular weight alkyl radicals.

7. A method for protecting the skin from the effects of UV radiation as claimed in claim 5, wherein $R^3$ to $R^8$ are hydrogen, and X is oxygen and Y is $=CR^9R^{10}$, where $R^9$ and $R^{10}$ are hydrogen or alkyl radicals having from 1 to 5 carbon atoms.

8. A method for protecting the skin from the effects of UV radiation as claimed in claim 5, wherein $R^1$ and/or $R^2$ are the radicals ethoxycarbonyl, acetyl or cyano, $R^3$ is hydrogen or methyl, $R^4$ is hydrogen or methyl, $R^5$ to $R^8$ are hydrogen, X is oxygen or $=C(CH_3)_2$ and Y is $=CH_2$ or $=C(CH_3)_2$.

* * * * *